United States Patent [19]

Milder et al.

[11] Patent Number: 4,902,272
[45] Date of Patent: Feb. 20, 1990

[54] INTRA-ARTERIAL CARDIAC SUPPORT SYSTEM

[75] Inventors: Fredric L. Milder, Brookline; Robert T. V. Kung, Andover; David M. Lederman, Marblehead; Param I. Singh, Lexington, all of Mass.

[73] Assignee: Abiomed Cardiovascular, Inc., Danvers, Mass.

[21] Appl. No.: 63,648

[22] Filed: Jun. 17, 1987

[51] Int. Cl.[4] .............................................. A61B 19/00
[52] U.S. Cl. ....................................... 600/18; 600/16; 600/17
[58] Field of Search ................. 128/1 D, 344; 604/96, 604/97, 98, 99, 100, 101

[56] References Cited

U.S. PATENT DOCUMENTS

| | | | |
|---|---|---|---|
| 2,854,983 | 10/1958 | Baskin | 128/349 |
| 3,266,487 | 8/1966 | Watkins et al. | 128/1 D |
| 3,376,660 | 7/1965 | McGinnis | 35/17 |
| 3,504,662 | 4/1970 | Jones | 128/1 D |
| 3,592,184 | 7/1971 | Watkins | 128/1 R |
| 3,692,018 | 9/1972 | Goetz et al. | 128/1 D |
| 3,709,227 | 1/1973 | Hayward | 128/351 |
| 3,718,044 | 2/1973 | Joyce, Jr. et al. | 73/223 |
| 3,939,820 | 2/1976 | Grayzel | 128/1 D |
| 4,077,394 | 5/1978 | McCurdy | 128/1 D |
| 4,080,958 | 3/1978 | Bregman et al. | 128/1 D |
| 4,154,227 | 5/1929 | Krause et al. | 128/1 D |
| 4,329,993 | 5/1982 | Lieber et al. | 128/349 |
| 4,407,271 | 10/1983 | Schiff | 128/1 D |
| 4,423,725 | 1/1984 | Baran et al. | 128/207 |
| 4,465,063 | 8/1984 | Nielsen et al. | 128/1 D |
| 4,522,195 | 6/1985 | Schiff | 128/1 D |
| 4,531,936 | 7/1985 | Gordon | 604/49 |
| 4,546,759 | 10/1985 | Solar | 128/1 D |
| 4,636,195 | 1/1987 | Wolinsky | 604/101 |
| 4,692,148 | 9/1987 | Kontrowitz et al. | 604/96 |
| 4,697,574 | 10/1987 | Karcher et al. | 128/1 D |

FOREIGN PATENT DOCUMENTS

| | | | |
|---|---|---|---|
| 0209070 | 1/1987 | European Pat. Off. | 128/1 D |
| 2658104 | 12/1977 | Fed. Rep. of Germany . | |
| 0244694 | 4/1987 | German Democratic Rep. | 604/99 |
| 2004942 | 4/1979 | United Kingdom . | |

OTHER PUBLICATIONS

USSR Inventor's Certificate No. 733,688, 5-15-1983, Shumakov et al.

Primary Examiner—C. Fred Rosenbaum
Assistant Examiner—Adam Cermak
Attorney, Agent, or Firm—Lahive & Cockfield

[57] ABSTRACT

An intra-arterial cardiac support system including multiple balloons for placement in the descending aorta with one balloon serving as a pumping balloon and one or more balloons serving as valve balloons, at least one of the valve balloons being positioned distal to the natural heart. The balloons are individually inflated and deflated to provide for sequential pumping action, with the sequence operating in timed relation to the sytstole and diastole of the natural heart.

13 Claims, 4 Drawing Sheets

INPUT FROM
R WAVE DETECTOR
OR PACEMAKER

CONTROL & DRIVE

4,902,272

INTRA-ARTERIAL CARDIAC SUPPORT SYSTEM

RELATED APPLICATION

This application is related to pending application, Ser. No. 008,061, filed Jan. 14, 1987, entitled High Frequency Intra-Arterial Support System, assigned to the same assignees this application is assigned to.

BACKGROUND OF THE INVENTION

This invention relates generally to temporary cardiac assist devices used to assist the operation of a failing, traumatized or infarcted heart for a limited period until either the heart recovers or more definitive treatment can be provided. In particular, it relates to so-called intra-aortic balloon pumps. Such a pump does not require major thoracic surgery to connect it to the circulation but is a collapsible structure which may be introduced into an easily accessible artery, such as a femoral, and may then be guided into some portion of the aorta, where it can be employed to assist the left side of the heart. In the usual "counterpulsation" mode of employment, the balloon is pneumatically inflated during diastole to increase blood pressure and deflated during systole to lower the pressure load upon the ventricle. This device and its mode of operation was described in a paper by Moulopolous, Topaz and Kolff, "Diastolic Balloon pumping in the Aorta—A Mechanical Assistance to the Failing Circulation", American Heart Journal (1962) 63, p. 669.

Since intra-aortic balloon pumps can be applied with relatively minor surgery and fairly standard vascular catheterization procedures, and afford some useful assistance to the left heart, they are well regarded. However, they provide much less pumping assistance than one would desire, for at least three reasons: first, the conveniently available volume within the aorta is not large compared to the desired stroke volume of the heart, particularly because of the necessity to avoid occluding important arteries such as the carotids and renals; second, the elastic compliance of the aortic wall makes the effective displacement of the balloon less than its geometric displacment, and third, the balloon is merely a phase shift device and not by itself, a true pump. Many inventions have been addressed to the alleviation of these problems: For example, U.S. Pat. No. 3,054,662 to R. T. Jones shows how to attain better pump fluid dynamics, and U.S. Pat. No. 3,692,018 to Goetz and Goetz shows how to direct the limited available flow predominantly to the critical brain and heart circulations. Although this limits the pump's effectiveness, the balloon pump is placed within the descending aorta in order that emboli which may be produced do not pass up the carotid arteries to the brain.

SUMMARY OF THE INVENTION

It is an object of this invention to provide an intra-arterial cardiac support system which will be positioned in the descending aorta to provide extracorporeally controlled balloon pumping.

It is another object of this invention to provide a balloon pumping support system in the descending aorta in which the pumping action is peristaltic in nature and operated in phased relationship to the systole and diastole of the natural heart. Broadly speaking, in the present invention an inflatable pumping balloon is inserted into the descending aorta, together with a separately controlled inflatable balloon valve positioned on the distal side of the pumping balloon from the aortic root. An extracorporeal control system is then used to inflate the balloons in timed relationship with the systole and diastole of the heart to pump blood away from the heart into the lower arterial system during systole and toward the heart during diastole. In a second embodiment, a third balloon, the inflation of which is controlled separately from that of the first two, is placed on the proximal side of the pumping balloon and all three balloons are inflated in a controlled sequence to effect peristaltic pumping which reverses direction several times during each natural heart beat.

DESCRIPTION OF PREFERRED EMBODIMENTS

Figure 1:
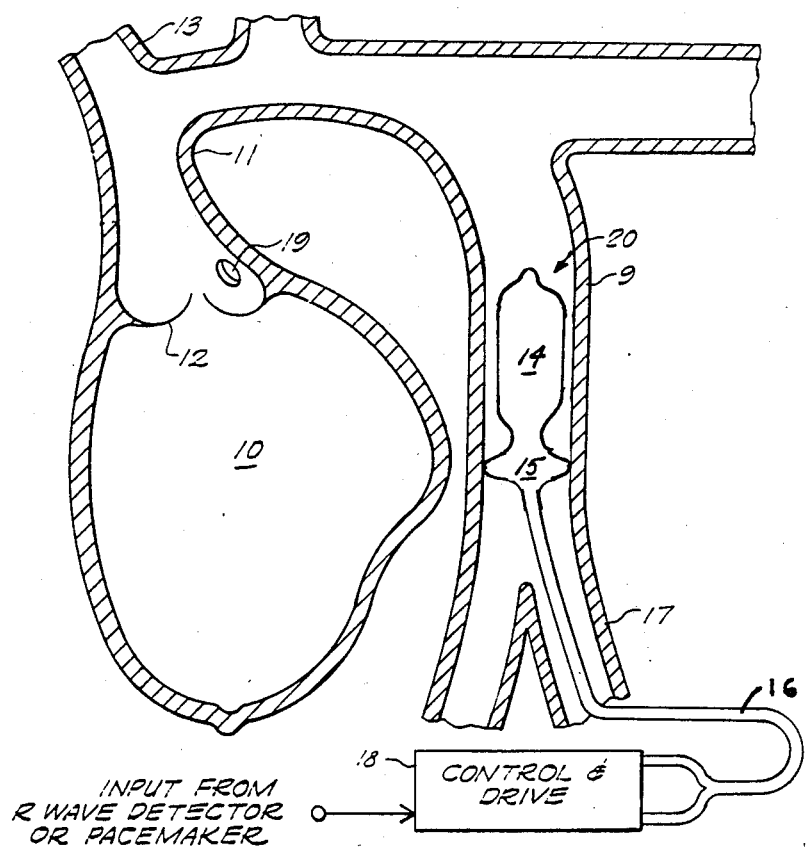
FIG. 1 is a schematic view of one embodiment of the intra-arterial cardiac support system of this invention incorporating two inflatable balloons.

FIG. 1 is a schematic view of the two balloon embodiment of the cardiac support system positioned in the descending aorta 9. Also shown is the left ventricle 10, the aortic root 11, the aortic valve 12, and a coronary artery 19.

In FIG. 1, left ventricle 10 is assisted by balloon pump 20 located in the descending aorta 9. Pump 20 comprises pumping balloon 14 and valve balloon 15 downstream from balloon 14, both attached to multi-lumen catheter 16 which is bought outside the body through the arterial tree, as via femoral artery 17 in FIG. 1.

Figure 2:
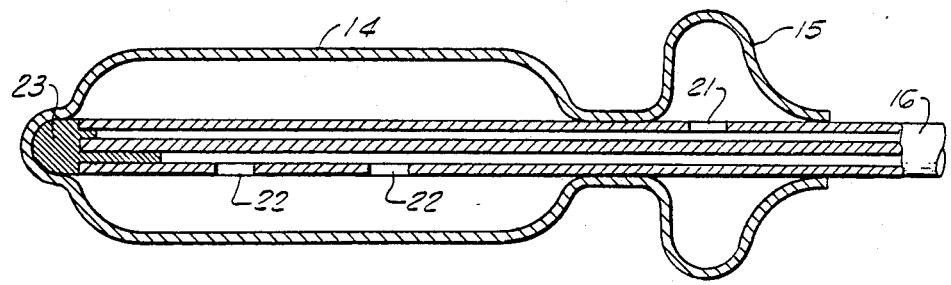
FIG. 2 is a cross-section view of a preferred embodiment of the balloon pump of this invention as used in the embodiment illustrated in FIG. 1.

Pump 20, as seen more particulary in FIG. 2, comprises a shaped hollow tubular body of thin elastomeric material cemented to multi-lumen catheter 16 to form pumping balloon 14 and valve 15. The end of balloon 14 is supported, by support 23, which may advantageously be made of radio-opaque material to facilitate placement of the device. The interior of pumping balloon 14 is connected fluidically to one lumen of catheter 16 by holes 22, and the interior of valve 15 is connected fluidically to the other lumen by hole(s) 21. In the drawings, dimensions such as thicknesses have been exaggerated in the interest of clarity.

Referring again to FIG. 1, it is seen that the outside diameter of valve balloon 15, when erected by inflation, should be just sufficient to substantially occlude descending aorta 9, and the outside diameter of pumping balloon 14 should be somewhat less. Clearly, a number of sizes will be needed to fit the population of potential patients. In most adults, the inside diameter of the descending aorta is of the order of 2.0 centimeters, and a suitable length for the balloon pump is of the order of 25.0 centimeters. The total displacement of the pumping balloon 14 when inflated, typically 40 cc, is between one half and one times the volume of a normal heart stroke. A suitable volume for the valve balloon 15 is 5 to 10 cc.

It can also be seen that the multi-lumen catheter 16 is connected to control and drive mechanism 18 which cyclically and individually inflates and deflates balloon 14 and balloon valve 15 by fluid flow through lumens of catheter 16. Although only two lumens are shown, it is customary to include an extra lumen to provide for insertion of the catheter over a guide and to use for pressure measurements after insertion. The elements of such control and drive mechanisms are well known in the art, but the specific sequence of operation is novel. In particular, the timing of inflation and deflation of the valve balloon in relation to that of the pumping balloon and to the natural heart cycle is arranged so that blood is pumped toward the aortic root during diastole and toward the lower arterial system during systole.

An input signal is provided to the control and drive unit 18 indicating when the systolic and diastolic periods of the patient's heart begin. This signal can be taken, for example, from the R wave of an electrocardiagraph. In other instances, where the patient's heart action is regulated by a pacemaker, the signals indicative of the systolic and diastolic periods may be obtained from the pacemaker itself. Further, if electrical timing signals are particularly troublesome, signals for the timing of the control unit may be obtained from arterial or ventricular pressure waveforms.

Figure 3:
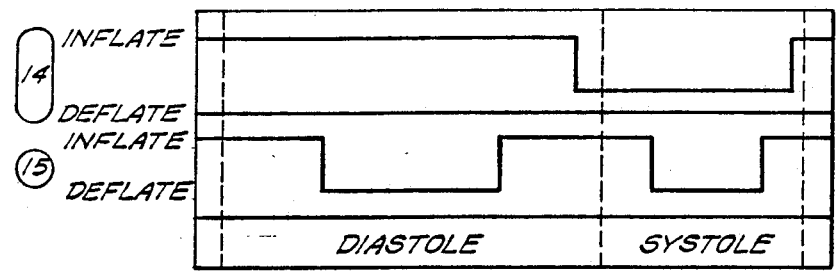
FIG. 3 is a timing diagram illustrating signals used to control the operation of the balloon pump of FIGS. 1 and 2.
Figure 3A:
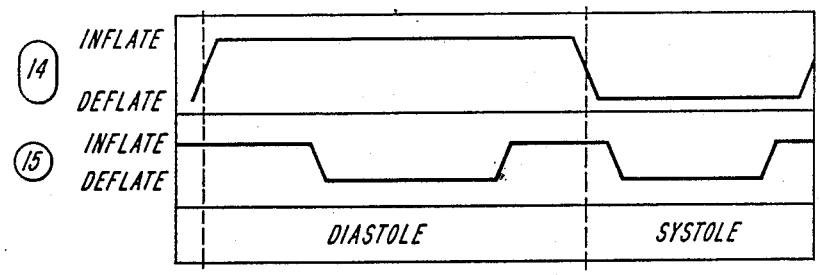
FIG. 3a is a timing diagram illustrating the timing of the actual inflation and deflation of the balloons in relation to the diastole and systole of the natural heart.

FIG. 3 illustrates a timing diagram for signals controlling the inflation and deflation of the pump balloon 14 and the distal balloon 15 suitable to accomplish the pumping. As illustrated in FIG. 3a, the actual transitions of the balloon from one state to the other occur after a delay occasioned by the pneumatic resistance of the pumping system and the catheter lumens as well as the compliance of the artery. At the beginning of the diastolic period the distal balloon 15 is inflated, thus blocking blood flow to the lower arterial system. When the pump balloon 14 inflates, this increases the blood pressure in that area causing blood flow back towards the aortic root 11. During diastole, the distal balloon is deflated for some period of time (which may in fact be zero) to allow additional perfusion of the lower arterial tree beyond that obtained during systole. The active control of the distal balloon through a separate lumen is essential to combining the maximal unloading of the ventricle, maximal coronary perfusion and control of the quantity of blood flowing to the lower aorta. At the end of diastole the pump balloon deflates and thereafter the distal valve balloon deflates. As a result, the blood pressure in the area of the pump is reduced, unloading the ventricle, and the distal valve balloon 15 allows blood to pass from the heart during its systolic action down through the descending aorta to the lower arterial system. Before the end of systole, the distal balloon 15 is reinflated and thereafter the pumping balloon 14 is reinflated to again commence the cycle.

Figure 4:
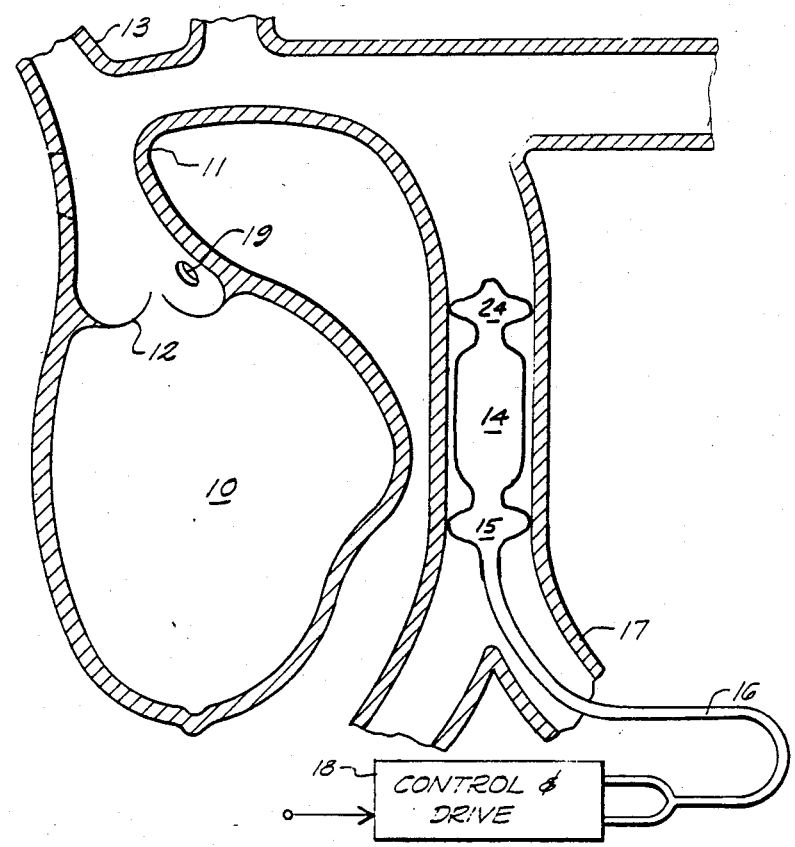
FIG. 4 is a schematic view of a second embodiment of the intra-arterial cardiac support system of this invention incorporating a pumping balloon and two valve balloons.
Figure 5:
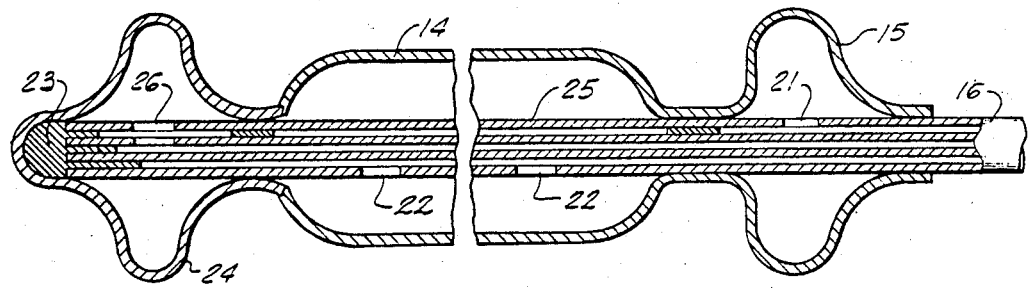
FIG. 5 is a cross-section view of a preferred embodiment of the balloon pump of this invention as used in the embodiment illustrated in FIG. 4.

In FIG. 4 there is illustrated an alternative embodiment in which three balloons are employed. In addition to the pumping balloon 14 and the distal valve balloon 15, there is included a proximal valve balloon 24. As illustrated in FIG. 5 a triple lumen catheter 25 provides for separately controllable inflation and deflation of all three balloon segments. The balloon segment 24 is controlled by gas flow through lumen 26 in the catheter 25. Again, in this configuration, the relative timing of the inflation and deflation of the three balloon segments 14, 15 and 24 with respect to each other, and with respect to the diastole and systole of the patient's heart, is such that peristaltic pumping is provided to cause blood flow in a direction toward the aortic root during diastole and away from the aortic root toward the lower arterial system during systole.

Figure 6:
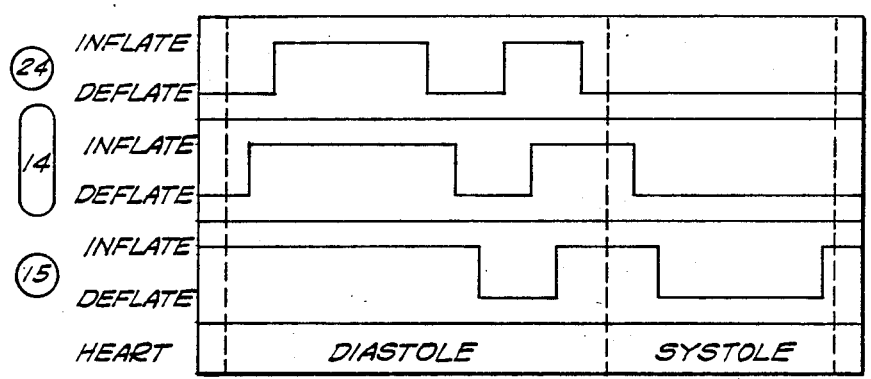
FIG. 6 is a timing diagram illustrating one sequence of operation of the balloon pump of FIGS. 4 and 5.
Figure 7:
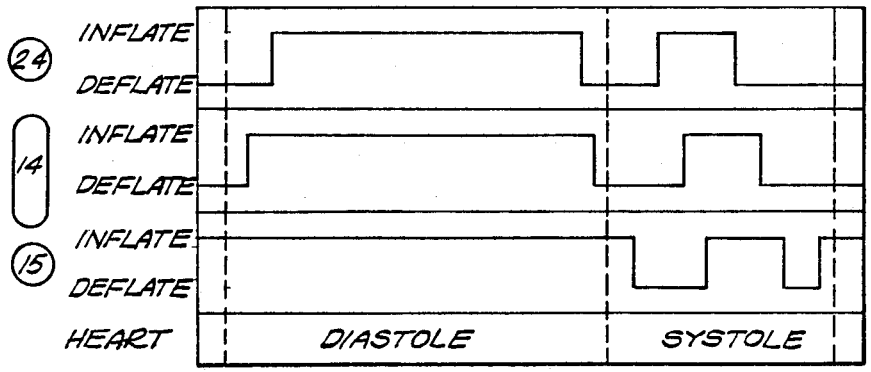
FIG. 7 is a timing diagram illustrating a different sequence of operation of the balloon pump of FIGS. 4 and 5.

FIGS. 6 and 7 illustrate timing diagrams for two suitable cyclical operations of the embodiment of FIG. 4. In FIG. 6 at the commencement of diastole distal balloon 15 is inflated, thus blocking blood flow to the lower arterial system. The proximal balloon 24 is deflated and hence inflation of the pump balloon 14 increases pressure and produces a flow toward the aortic root 11. The proximal balloon 24 next inflates, producing a condition in which all three balloons are inflated, further increasing pressure in the aortic root. During this phase, perfusion of the coronary arteries is accomplished.

Next, near the end of diastole, deflation of the proximal balloon is followed by deflaton of the pump balloon moving blood away from the aortic root. Then the distal balloon is deflated and the proximal balloon is reinflated, blocking blood flow from the aortic root. The pump balloon 14 is then inflated, forcing blood into the lower arterial tree. Distal balloon 15 inflates to prevent backflow and then the sequential deflation of proximal balloon 24, pump balloon 14 and distal balloon 15 lowers the pressure in the aortic root and further allows for blood flow under the systolic action of the heart through the descending aorta to the lower arterial system.

In FIG. 7 a similar timing sequence is shown, which produces however peristaltic pumping during systole through the descending aorta toward the lower arterial system. Note that in both configurations, the pumping balloon inflates more than once during each heartbeat, in contrast to the usual counterpulsation mode of other intra-aortic balloon pumps.

While specific timing sequences and configurations have been illustrated, it will be realized that the invention in both embodiments may be also configured and timed in alternative forms. In particular, placement of the balloons on catheters may be reversed so as to facilitate introduction into the descending aorta from the subclavian artery. Additional timing sequences may involve multiple repetitions of segments of the specific diagrams shown in order to enhance the effect of that timing segment relative to the entire cycle.

I claim:

1. A pumping system for assisting the pumping of a natural heart comprising,
   a first pumping balloon having a volume greater than about one-half times the volume of the natural heart stroke, for positioning within the descending aorta;
   a second balloon for positioning within said aorta on the distal side of said first balloon, the distal side being the side furthest from the heart when said balloon is positioned within said descending aorta, said second balloon, when inflated being large enough to substantially block blood flow from the upper aorta to the lower arterial system, catheter means for insertion from outside of the patient's body connecting to said balloons providing gas flow to selectively inflate either of said first and second balloons, and control means responsive to signals indicative of the beginning of systole and diastole of said heart to control the inflation of said first and second balloons in sequence so as to provide pumping away from said heart during the systole of the natural heart and toward said heart during diastole of said heart.

2. A system in accordance with claim 1 wherein said control means is responsive to R waves generated by the natural heart or from arterial pressure waveforms as indications of systole and diastole in said heart.

3. A pumping system for assisting the pumping of a natural heart comprising, a first pumping balloon having a volume greater than about one-half times the volume of the natural heart stroke, for positioning within the descending aorta;

a second balloon for positioning within said aorta on the distal side of said first balloon, the distal side being the side furthest from the heart when said balloon is positioned within said descending aorta, said second balloon, when inflated being large enough to substantially block blood flow from the upper aorta to the lower arterial system, catheter means for insertion from outside of the patient's body connecting to said balloons providing gas flow to selectively inflate either of said first and second balloons, and control means responsive to signals indicative of the beginning of systole and diastole of said heart to control the inflation of said first and second balloons in sequence so as to provide during systole said first pumping balloon is inflated after inflation of said second balloon and thereafter said first pumping balloon is deflated while said second balloon is still inflated and, after deflation of said first pumping balloon, said second balloon is deflated.

4. A system in accordance with claim 3 wherein during diastole said second balloon is deflated while said first balloon is in an inflated state.

5. A pumping system for assisting the pumping of a natural heart comprising, a first pumping balloon having a volume greater than about one-half times the stroke volume of the natural heart, for positioning within the descending aorta;

a second balloon for positioning within said aorta on the distal side of said first balloon, the distal side being the side furthest from the heart when said balloon is positioned within said descending aorta, said second balloon, when inflated being large enough to substantially block blood flow from the upper aorta to the lower arterial system, a third balloon positioned within said aorta on the proximal side of said first balloon, the proximal side being the side of the first balloon closest to the heart when that balloon is positioned within the descending aorta, said third balloon when inflated being large enough to substantially block blood flow from the upper aorta to the lower arterial system;

catheter means for insertion from outside of the patient's body connecting to said balloons providing gas flow to selectively inflate any of said first, second and third balloons, and control means responsive to signals indicative of the beginning of systole and of diastole of said natural heart to control the inflation of said first, second and third balloons in sequence so as to provide peristaltic pumping away from said heart during the systole of said heart and toward said heart during diastole of said heart.

6. A system in accordance with claim 5 wherein said control means provides that during systole said first balloon is deflated only when said third balloon has previously been deflated and while said second balloon is in an inflated state and thereafter said second balloon is deflated.

7. A system in accordance with claim 5 wherein said control means provides that during diastole inflation of said first balloon takes place at least once while said second balloon is in an inflated state and said third balloon is in a deflated state.

8. A system in accordance with claim 5 wherein said control means provides that during diastole said first balloon is deflated only when said third balloon has previously been deflated and while said second balloon is in an inflated state and thereafter said second balloon is deflated.

9. A system in accordance with claim 1 wherein said control means provides that there are a plurality of cycles of inflation and deflation of said balloons during systole of said heart.

10. A system in accordance with claim 5 wherein said control means is responsive to R waves generated by the natural heart or from arterial pressure waveforms as indications of systole and diastole in said heart.

11. A pumping system for assisting the pumping of a natural heart comprising, a first pumping balloon having a volume greater than about one-half times the volume of the natural heart stroke, for positioning within the descending aorta;

a second balloon for positioning within said aorta on the distal side of said first balloon, the distal side being the side furthest from the heart when said balloon is positioned within said descending aorta, said second balloon, when inflated being large enough to substantially block blood flow from the upper aorta to the lower arterial system, catheter means for insertion from outside of the patient's body connecting to said pumping means providing gas flow to selectively inflate either of said first and second balloons, and control means responsive to signals indicative of the beginning of systole and diastole of said heart to control the inflation of said first and second balloons in sequence so as to provide pumping away from said heart during the systole of the natural heart and toward said heart during diastole of said heart, wherein said control means provides that there are a plurality of cycles of inflation and deflation of said balloons during systole of said heart.

12. A pumping system for assisting the pumping of a natural heart comprising, a first pumping balloon having a volume greater than about one-half times the stroke volume of the natural heart, for positioning within the descending aorta;

a second balloon for positioning within said aorta on the distal side of said first balloon, the distal side being the side furthest from the heart when said balloons is positioned within said descending aorta, said second balloon, when inflated being large enough to substantially block blood flow from the upper aorta to the lower arterial system, a third balloon positioned within said aorta on the proximal side of said first balloon, the proximal side being the side of the first balloon closest to the heart when that balloon is positioned within the descending aorta, said third balloon when inflated being large enough to substantially block blood flow from the upper aorta to the lower arterial system;

catheter means for insertion from outside of the patient's body connecting to said balloons providing gas flow to selectively inflate any of said first, second and third balloons, control means responsive to signals indicative of the beginning of systole and of diastole of said natural heart to control the inflation of said first, second and third balloons in sequence so as to provide peristaltic pumping away from said heart during the systole of said heart and toward said heart during diastole of said heart, and wherein said control means provides a controlled sequence of inflation such that during systole inflation of said first balloon takes place while said second balloon is deflated and said third balloon is in an inflated state.

13. A pumping system for assisting the pumping of a natural heart comprising, a first pumping balloon having a volume greater than about one-half times the stroke volume of the natural heart, for positioning within the descending aorta;

a second balloon for positioning within said aorta on the distal side of said first balloon, the distal side being the side furthest from the heart when said balloon is positioned within said descending aorta, said second balloon, when inflated being large enough to substantially block blood flow from the upper aorta to the lower arterial system, a third balloon positioned within said aorta on the proximal side of said first balloon, the proximal side being the side of the first closest to the heart when that balloon is positioned within the descending aorta, said third balloon when inflated being large enough to substantially block blood flow from the upper aorta to the lower arterial system;

catheter means for insertion from outside of the patient's body connecting to said balloons providing gas flow to selectively inflate any of said first, second and third balloons, control means responsive to signals indicative of the beginning of systole and of diastole of said natural heart to control the inflation of said first, second and third balloons in sequence so as to provide peristaltic pumping away from said heart during the systole of said heart and toward said heart during diastole of said heart, and wherein said control means provides a controlled sequence of inflation such that during diastole inflation of said first balloon takes place while said second balloon is deflated and said third balloon is in an inflated state.

* * * * *

UNITED STATES PATENT AND TRADEMARK OFFICE
CERTIFICATE OF CORRECTION

PATENT NO. : 4,902,272

DATED : February 20, 1990

INVENTOR(S) : Fredric L. Milder, Robert T. V. Kung, David M. Lederman, and Param I. Singh It is certified that error appears in the above-identified patent and that said Letters Patent is hereby corrected as shown below:

Column 8, line 14 after "first" insert --balloon--.

Signed and Sealed this

Eighth Day of December, 1992

*Attest:*

DOUGLAS B. COMER

*Attesting Officer*     *Acting Commissioner of Patents and Trademarks*